United States Patent
Megerle et al.

[11] Patent Number: 6,100,698
[45] Date of Patent: Aug. 8, 2000

[54] ION MOBILITY SENSORS AND SPECTROMETERS HAVING A CORONA DISCHARGE IONIZATION SOURCE

[76] Inventors: Clifford A. Megerle, 4014 Corte Cancion, Thousand Oaks, Calif. 91360; David B. Cohn, 4221 Mesa St., Torrance, Calif. 90505

[21] Appl. No.: 08/877,542
[22] Filed: Jun. 17, 1997
[51] Int. Cl.$^7$ .................................................. G01N 27/62
[52] U.S. Cl. .......................................... 324/464; 250/286
[58] Field of Search .................................. 324/464, 459, 324/71.1; 250/286, 287, 292

[56] References Cited

U.S. PATENT DOCUMENTS

| | | | |
|---|---|---|---|
| 4,551,624 | 11/1985 | Spangler | 250/287 |
| 5,047,723 | 9/1991 | Puumalainen | 324/464 |
| 5,420,424 | 5/1995 | Carnahan | 250/287 |
| 5,684,300 | 11/1997 | Taylor | 250/286 |

*Primary Examiner*—Maura Regan

[57] ABSTRACT

A chemical sensor comprising a gas detector having first and second printed wiring boards with opposed separated pairs of signal and grounded counter electrodes and processing electronics for processing ionic current signals derived from the signal and counter electrodes. A corona discharge source is provided that produces an ionized air stream containing a chemical that is to be detected. An insulating plate is disposed between the second printed wiring board of the gas detector and the corona discharge source that is used to electrically isolate the electrodes and processing electronics of the gas detector from the corona discharge source. An air flow passage is formed through the corona discharge source, the insulating plate, and the gas detector that allows the ionized air stream generated by the corona discharge source to flow past the signal and counter electrodes, so that the chemical may be detected.

12 Claims, 2 Drawing Sheets

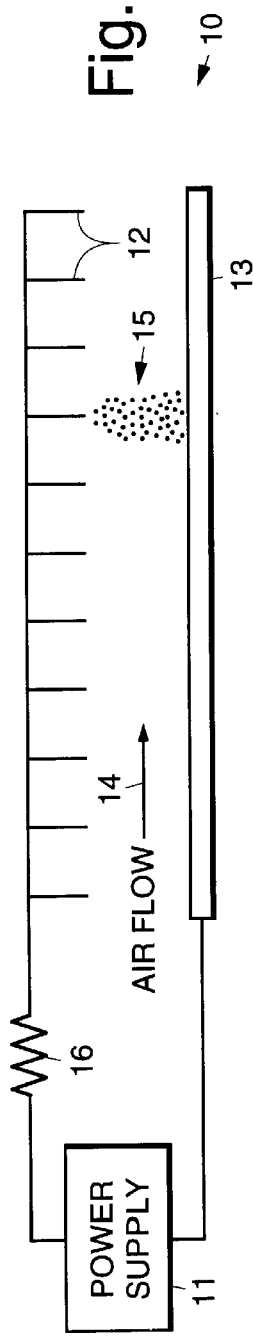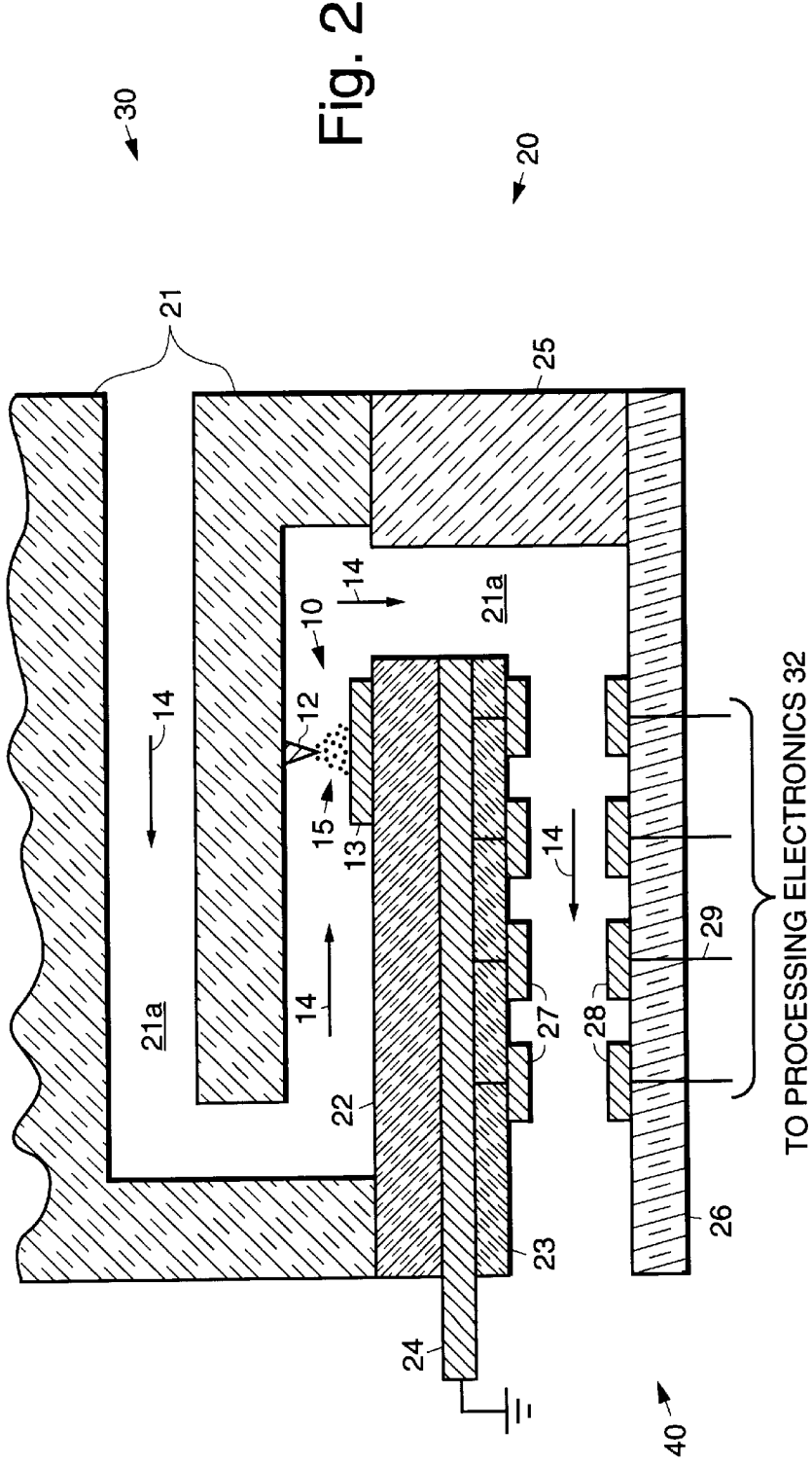

ION MOBILITY SENSORS AND SPECTROMETERS HAVING A CORONA DISCHARGE IONIZATION SOURCE

GOVERNMENT RIGHTS

The present invention was developed under Contract No. F08626-94-C-0029 awarded by the Department of the Air Force. The United States Government has certain rights in this invention.

BACKGROUND

The present invention relates generally to ion mobility spectrometers and sensors, and more particularly, to ion mobility sensors and spectrometers employing corona discharge ionization sources that are used as chemical sensors.

All known commercially available ion mobility spectrometers and sensors use isotopic ionization sources. One such ion mobility spectrometer is disclosed in U.S. Pat. No. 5,047,723 entitled "Method for Detection of Foreign Matter Contents in Gases", issued Sep. 10, 1991, for example. This patent discloses the use of an ionized carrier gas containing foreign matter that is passed through chambers with different electric fields. The field currents passing through two or more chambers are measured, and corresponding signals are obtained. The amounts and relationships of these signals permit analysis of the foreign matter contained in the gasses. The ionization source disclosed in this patent is an isotopic ionization source wherein radioactive radiation derived from an Americium ionization source ionizes the carrier gas and the molecules of the foreign matter contained in it.

Isotopic materials are subject to regulation, and analysis devices, including detection devices implementing the method disclosed in the above-cited patent are not well-received by users, particularly because of the isotopic nature of the devices. In particular, U.S. government facilities are very reluctant to use ion mobility spectrometers that use isotopic ionization sources.

Therefore, it would be an advantage to have an ion mobility spectrometer that does not use an isotopic ionization source. Accordingly, it is an objective of the present invention to provide for an ion mobility spectrometer that employs a corona discharge ionization source.

SUMMARY OF THE INVENTION

To meet the above and other objectives, the present invention provides for an ion mobility spectrometer having a corona discharge ionization source. The ion mobility spectrometer includes a chemical sensor comprising a gas detector having first and second printed wiring boards with opposed separated pairs of signal and grounded counter electrodes, and processing electronics for processing ionic current signals derived from the signal and counter electrodes.

A corona discharge source is provided that produces an ionized air stream containing a chemical that is to be detected. The corona discharge ionization source comprises a power supply, with one or more positive electrodes separated from a negative ground electrode, and which are coupled to the power supply. However, it is to be understood that the corona discharge ionization source may have either polarity.

An insulating plate is disposed between the second printed wiring board of the gas detector and the corona discharge source that is used to physically and electrically isolate the electrodes and processing electronics of the gas detector from the corona discharge source and its high voltage. An air flow passage is formed through the corona discharge source, the insulating plate, and the gas detector that allows the ionized air stream generated by the corona discharge source to flow past the signal and counter electrodes, so that the chemical may be detected.

The corona discharge ionization source replaces a Nickel 63 or an Americium 241 isotopic ionization source used in conventional ion mobility sensors and spectrometers, such as a model M-90 chemical warfare agent monitor manufactured by Environics OY, located in Finland. The present invention replaces the isotopic material currently used to ionize gases in virtually all ion mobility spectrometers with a non-isotopic, high-performance ion source.

The present corona discharge ionization source produces many more ions than typical isotopic ionization sources, and, in some applications, thus provides for a spectrometer having a higher sensitivity and/or wider dynamic range for detecting chemical warfare agent species in high concentrations. The present invention is well-suited for use in hand-held monitors that detect hazardous chemicals in air. Such monitors have wide applicability, including military, industrial and commercial applications.

BRIEF DESCRIPTION OF THE DRAWINGS

The various features and advantages of the present invention may be more readily understood with reference to the following detailed description taken in conjunction with the accompanying drawings, wherein like reference numerals represent like structural elements, and in which FIG. 1 illustrates a corona discharge ionization source in accordance with the principles of the present invention;

FIG. 2 illustrates a reduced to practice embodiment of the corona discharge ionization source that was built to test out the principles of the present invention;

DETAILED DESCRIPTION

Figure 3:
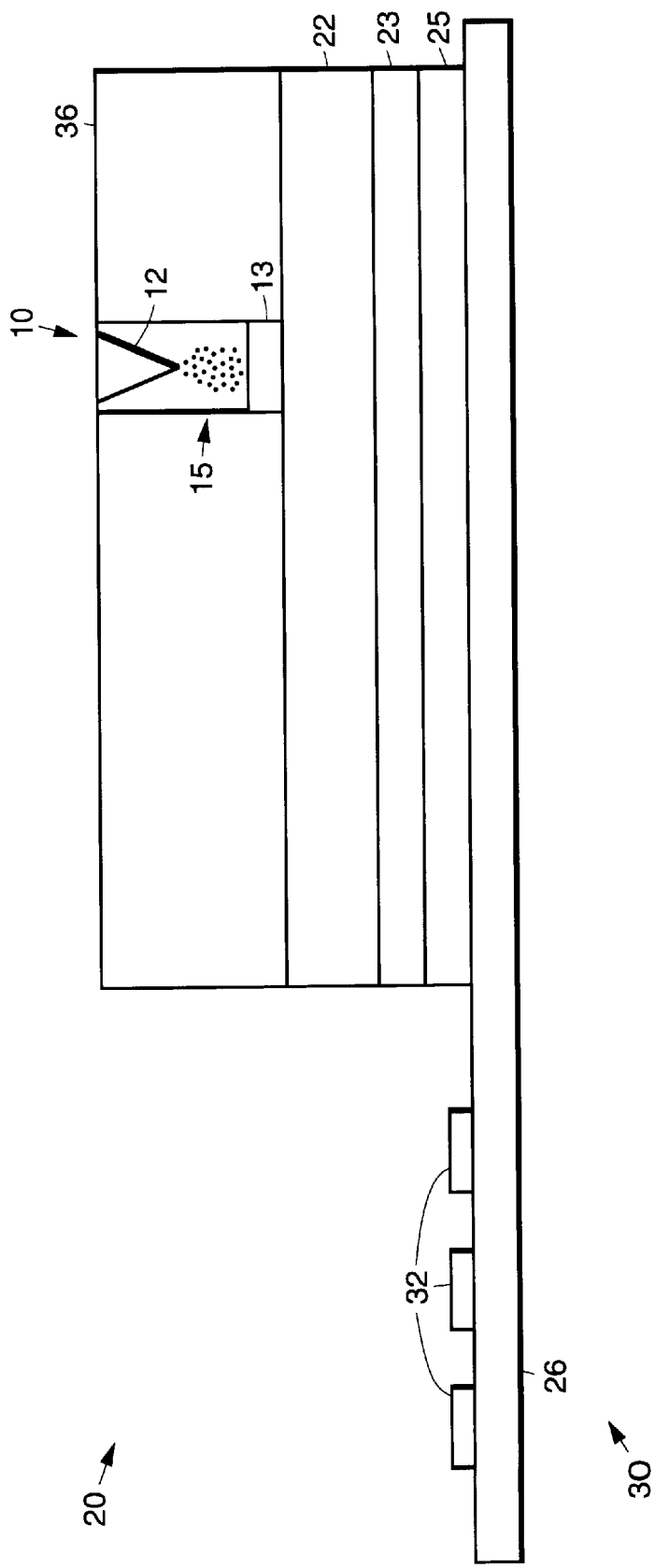
FIG. 3 illustrates an ion mobility spectrometer employing the present corona discharge source.

Referring to the drawing figures, FIG. 1 illustrates corona discharge ionization source 10 in accordance with the principles of the present invention. The corona discharge ionization source 10 comprises a power supply 11, which may be a battery, for example, having a positive electrode coupled to one or more positive or first electrodes 12. The first electrode 12 or electrodes 12 may be fabricated as a sharp metallic corona point 12, or multiple sharp metallic corona points 12. A preferred embodiment of the corona discharge ionization source 10 uses a linear array of positive or first electrodes 12. A negative electrode of the power supply 11 is coupled to a ground plane 13 or second electrode 13 disposed adjacent to the linear array of first electrodes 12, and displaced therefrom by a predetermined distance so that there is an air gap therebetween. However, it is to be understood that the corona discharge ionization source 10 may have the opposite polarity from the disclosed embodiment.

In order to ensure that the corona discharge ionization source 10 works well, it is important to have a large series resistor 16 disposed between the power supply 11 (high voltage source) and the electrodes 12. This resistor 16 is typically greater than one megohm, and a 12 megohnm resistor 16 was used in the preferred embodiment of the corona discharge ionization source 10. The purpose of the resistor 16 is to limit the current flow to ensure that the low current corona discharge produced by the corona discharge ionization source 10 does become a high current arc or spark discharge.

A high voltage (typically on the order of from 1500 to 3000 volts) is applied across the electrodes 12, 13 which creates a discharge 15 of positive and negative ions in the air gap therebetween. Each of the corona points 12 or first electrodes 12 supports a separate discharge 15. An air stream 14 is caused to move past the electrodes 12, 13 which produces a flow of ionized air. The corona discharge ionization source 10 may be advantageously used as part of an ion mobility spectrometer 20 or sensor 20 that will be described with reference to FIGS. 2 and 3.

The corona discharge source 10 is based on a discharge in air between the sharp metallic corona point 12, or points 12 comprising the first electrode(s) 12, and the ground plane 13 or second electrode 13. In this compact geometry of a preferred embodiment, the metallic corona points 12 or first electrodes 12 are displaced approximately one to two millimeters away from the ground plane 13 and a one to two kilovolt direct current (DC) discharge is maintained between the electrodes 12, 13.

In this configuration, the corona discharge source 10 produces a discharge 15 that consumes only two to ten milliwatts of power. Although the discharge voltage is relatively high, the discharge current is very low, around five microamperes. As a result, the corona discharge source 10 has relatively low discharge power and produces a relatively low drain on the power supply 11.

The air stream 14 passes between the corona point(s) 12 and the ground plane 13, producing a discharge 15 containing positive and negative ions, which ions are also produced by conventional isotopic ionization sources. However, in the case of the corona discharge ionization source 10, the charged particle density in the discharge 15 is typically orders of magnitude higher than that produced by a small isotopic source, thereby greatly improving the signal to noise ratio and greatly increasing the sensitivity of a spectrometer or sensor in which it is employed.

FIG. 2 illustrates a reduced to practice embodiment of the corona discharge ionization source 10 that was built to test out the principles of the present invention.

The corona discharge ionization source 10 was integrated into a sensor cell 30 of an existing ion mobility spectrometer 20 or sensor 20. More particularly, a model M-90 sensor cell 30 of an ion mobility spectrometer 20 or sensor 20 manufactured by Environics OY was modified to replace the isotopic ionization source (Americium 241 source) used therein with the corona discharge ionization source 10.

As is shown in FIG. 2, the sensor cell 30 of the ion mobility spectrometer 20 or sensor 20 comprises a insulator block 21, which may be made of Teflon material, for example. The insulator block 21 has an air passage 21a disposed therethrough, through which an air stream 14 may flow. An insulating plate 22, such as an alumina plate 22, for example, is disposed adjacent to the insulator block 21 and forms a wall of the air passage 21a.

The corona discharge ionization source 10 is disposed within the air passage 21a between the insulator block 21 and the insulating plate 22. The first electrodes 12 of the corona discharge ionization source 10 are disposed adjacent to the insulator block 21, while the ground plane 13 or second electrode 13 is disposed adjacent to the insulating plate 22. The ionic discharge 15 is created between the electrodes 12, 13 in the air passage 21a when voltage is applied to the electrodes 12, 13. However, although the electrodes 12, 13 are shown as having a vertical orientation, it is to be understood that they may also be oriented horizontal (i.e., rotated 90° relative to the orientation shown in FIG. 2).

An insulating spacer 25, which may be made of Teflon material, for example, is disposed between the insulator block 21 and a first printed wiring board 26 upon which a plurality of ion current signal electrodes 28 are formed. The ion current signal electrodes 28 are coupled to processing electronics 32. A second printed wiring board 23 has a plurality of grounded counter electrodes 27 formed on one surface thereof which may be grounded or held at some specific voltage, and a ground plane 24 that is grounded may also be included. The ground plane 24 of the second printed wiring board 23 abuts the insulating plate 22.

The first and second printed wiring boards 26, 23 are separated from each other so that the signal and counter electrodes 28, 27 are spaced apart by a predetermined distance, and wherein part of the air passage 21a is formed between the printed wiring boards 26, 23. The respective ion current signal electrodes 28 and counter electrodes 27 face each other and are aligned in pairs. The ion current signal electrodes 28 are coupled to the processing electronics 32 and are used to detect the ion current present in the ionized air stream 14 that flows through the passage 21a. The first and second printed wiring boards 26, 23 and the spaced apart signal and counter electrodes 28, 27 and the processing electronics 32 form a gas detector 40. This corona discharge ionization source 10 may also be used in ion mobility spectrometers having a design different from that shown and described herein.

The air stream 14 flowing through the air passage 21a is ionized by the discharge 15 produced by the corona discharge ionization source 10. The ionized air stream 14 flows past each of the pairs of signal and counter electrodes 28, 27 which detect the ion current carried by the moving air stream 14. The ion current detected by the respective signal and counter electrodes 28, 27 may be processed in a conventional manner to determine the presence of different ionic species present in the ionized air stream 14.

The corona discharge source 10 and sensor cell 30 shown in FIG. 2 were reduced to practice by modifying a large Teflon insulator block 21 used in the Environics OY M-90 ion mobility spectrometer sensor cell 30, and by removing the Americium source therefrom. A metal pin electrode 12 was pushed into the Teflon insulator block 21 and a ground electrode 13 was fabricated using a copper foil strip having back-side adhesive that was attached to the top of the alumina insulating plate 22 at a location beneath the metal pin electrode 12. Also, an alternative ground electrode 13 was fabricated using a pin in the manner described above, which was pushed through the Teflon insulator block 21 from the opposite side. The spacing between the metal pin electrode 12 and the alumina insulating plate 22 was adjusted. The Teflon insulator block 21, alumina insulating plate 22, and ion mobility spectrometer cell 30 (comprising the signal and counter electrodes 28, 27 and their respective printed wiring boards 26, 23) were bolted together to form an integrated sensor cell 30 having the present corona discharge source 10.

The ion mobility spectrometer 20 or sensor 20 containing the present corona discharge source 10 was tested The results of this test were positive when voltages in excess of 1500 V were applied to the corona discharge electrode 12. An ion spectrum was measured when the Environics OY M-90 electronics were attached to the modified M-90 sensor cell. A nerve agent simulant known as dimethyl methyl phosphonate (DMMP) contained in the air stream 14 was detected during corona discharge ionization.

FIG. 3 illustrates a sensor portion of an ion mobility spectrometer 20 or sensor 20 employing the corona discharge source 10. The portion of an ion mobility spectrometer 20 or sensor 20 shown in FIG. 3 is referred to as a miniature cell 30. The miniature cell 30 of the ion mobility spectrometer 20 is similar in construction to a model M-90 ion mobility spectrometer sensor cell manufacture by Environics OY, but with two distinct differences, which will be explained below.

The miniature cell 30 of the ion mobility spectrometer 20 or sensor 20 shown in FIG. 3 has a first printed wiring board 26 configured as a base plate which contains the processing electronics 32 used to process ionic current signals derived from signal and counter electrodes 28, 27. A relatively small spacer block 25 is disposed on top of a portion of the first printed wiring board 26. A second printed wiring board 23 is disposed on top of the relatively small spacer block 25.

In the present miniature cell 30, a relatively thick insulating plate 22 is disposed on top of the second printed wiring board 23. The relatively thick insulating plate 22 has a thickness on the order of 3/16 inches, and is used to shield the signal and counter electrodes 28, 27 from the high discharge voltage produced by the corona discharge source 10. Typically, materials used to produce the second printed wiring board 23 are insufficient to properly shield the signal and counter electrodes 28, 27, and the use of the relatively thick insulating plate 22 insures that the signal and counter electrodes 28, 27 are isolated from the corona discharge source 10.

The signal and counter electrodes 28, 27 are attached to sensitive current amplifiers and low voltage power supplies (not shown) such as those used in the M-90 ion mobility spectrometer sensor cell, and as is discussed in U.S. Pat. No. 5,047,723, for example. The present corona discharge source 10 is fabricated using the relatively thick (3/16 inch) alpha-alumina insulating plate 22 that isolates the high voltage produced by the corona discharge source 10 from the signal and counter electrodes 28, 27 and the electronics attached thereto. The alpha-alumina insulating plate 22 is fabricated with holes that allow the air stream 14 to flow through it and into the area of the miniature cell 30 containing the signal and counter electrodes 28, 27.

The miniature cell 30 shown in FIG. 3 does not use the insulator block 21 used in the Environics OY model M-90 ion mobility spectrometer sensor cell. The present miniature cell 30 uses a corona discharge printed wiring board 36 that incorporates the corona discharge source 10 in place of the insulator block 21.

The ionized air stream 14 passes through the corona discharge printed wiring board 36 and into the analytical region of the ion mobility spectrometer cell. In this way, the distance from the corona discharge ionization source 10 to the analytical region containing the signal and counter electrodes 28, 27 is minimized, and is about the same as is the case in the Environics OY M-90 cell. The embodiment of the miniature cell 30 of FIG. 3 thus has a relatively low profile. The corona discharge source 10 thus provides a simple, low power, and compact means for producing ionized species for chemical sensors and spectrometers, and the like.

Thus, the present invention provides for a chemical sensor 20 comprising a gas detector 40, a corona discharge source 10 that produces an ionized air stream 14 containing a chemical that is to be detected, an insulating plate 22 disposed between the gas detector 40 and the corona discharge source 10 that electrically isolates them, and an air flow passage 21a formed through the corona discharge source 10, insulating plate 22, and gas detector 40 that allows the ionized air stream 14 to flow through the gas detector 40 so that the chemical may be detected.

Thus, an ion mobility spectrometer that may be used as a chemical sensor having a corona discharge ionization source has been disclosed. It is to be understood that the described embodiments are merely illustrative of some of the many specific embodiments which represent applications of the principles of the present invention. Clearly, numerous and other arrangements can be readily devised by those skilled in the art without departing from the scope of the invention.

What is claimed is:

1. An ion mobility sensor comprising:

a gas detector comprising:
   a first printed wiring board having a plurality of signal electrodes;
   a second printed wiring board having a plurality of grounded counter electrodes separated from the first printed wiring board; and
   processing electronics coupled to the signal and counter electrodes for processing ionic current signals derived therefrom;

a corona discharge source;

an insulating plate disposed between the second printed wiring board of the gas detector and the corona discharge source; and an air flow passage formed through the corona discharge source, the insulating plate, and the gas detector for permitting an ionized air stream generated by the corona discharge source to flow past the signal and counter electrodes.

2. The sensor of claim 1 wherein the corona discharge source is fabricated on a corona discharge printed wiring board.

3. The sensor of claim 1 wherein the corona discharge source is disposed in an insulator block disposed adjacent to the insulating plate.

4. The sensor of claim 3 wherein the insulator block comprises Teflon material.

5. The sensor of claim 1 wherein the insulating plate comprises an alumina plate.

6. The sensor of claim 1 wherein the first and second printed wiring boards are separated by an insulating spacer.

7. The sensor of claim 6 wherein the insulating spacer comprises Teflon material.

8. The sensor of claim 1 wherein the corona discharge ionization source comprises:

a power supply;

a first electrode coupled to the power supply; and a ground plane coupled to the power supply and disposed adjacent to the first electrode and displaced therefrom by a predetermined distance.

9. The sensor of claim 1 wherein the corona discharge ionization source comprises:

a power supply;

a first plurality of electrodes coupled to the power supply; and a ground plane coupled to the power supply and disposed adjacent to the first plurality of electrodes and displaced therefrom by a predetermined distance.

10. An ion mobility sensor comprising:
a gas detector comprising:
- a plurality of signal electrodes;
- a plurality of grounded counter electrodes separated from the first plurality of signal electrodes; and
- processing electronics coupled to the signal and counter electrodes for processing ionic current signals derived therefrom;

a corona discharge source;

an insulating plate disposed between the plurality of signal electrodes of the gas detector and the corona discharge source; and an air flow passage formed through the corona discharge source, the insulating plate, and the gas detector for permitting an ionized air stream generated by the corona discharge source to flow past the signal and counter electrodes.

11. The sensor of claim 10 wherein the corona discharge ionization source comprises:
- a power supply;
- a first electrode coupled to the power supply; and
- a ground plane coupled to the power supply and disposed adjacent to the first electrode and displaced therefrom by a predetermined distance.

12. The sensor of claim 10 wherein the corona discharge ionization source comprises:
- a power supply;
- a first plurality of electrodes coupled to the power supply; and
- a ground plane coupled to the power supply and disposed adjacent to the first plurality of electrodes and displaced therefrom by a predetermined distance.

* * * * *

UNITED STATES PATENT AND TRADEMARK OFFICE
CERTIFICATE OF CORRECTION

PATENT NO : 6,100,698
DATED : August 8, 2000
INVENTOR(S) : Clifford A. Megerle et al.

It is certified that error appears in the above-identified patent and that said Letters Patent are hereby corrected as shown below:

On the title page,

After "Inventors' Names" please insert:

Assignee: Raytheon Company, Lexington, MA

Signed and Sealed this

Seventeenth Day of April, 2001

*Attest:*

NICHOLAS P. GODICI

*Attesting Officer*     *Acting Director of the United States Patent and Trademark Office*